United States Patent
Mitsui et al.

(10) Patent No.: US 12,022,590 B2
(45) Date of Patent: Jun. 25, 2024

(54) ILLUMINATION DEVICE, ILLUMINATION SYSTEM, AND ILLUMINATION CONTROL METHOD

(71) Applicants: KYOCERA Corporation, Kyoto (JP); Public University Corporation Nara Medical University, Kashihara (JP)

(72) Inventors: Katsuhiro Mitsui, Ritto (JP); Hidetaka Katou, Omihachiman (JP); Kenji Obayashi, Kashihara (JP)

(73) Assignees: KYOCERA CORPORATION, Kyoto (JP); PUBLIC UNIVERSITY CORPORATION NARA MEDICAL UNIVERSITY, Kashihara (JP)

( * ) Notice: Subject to any disclaimer, the term of this patent is extended or adjusted under 35 U.S.C. 154(b) by 90 days.

(21) Appl. No.: 17/798,650

(22) PCT Filed: Feb. 19, 2021

(86) PCT No.: PCT/JP2021/006483
§ 371 (c)(1),
(2) Date: Aug. 10, 2022

(87) PCT Pub. No.: WO2021/167100
PCT Pub. Date: Aug. 26, 2021

(65) Prior Publication Data
US 2023/0156892 A1    May 18, 2023

(30) Foreign Application Priority Data
Feb. 19, 2020  (JP) ................................. 2020-026628

(51) Int. Cl.
*H05B 47/16*    (2020.01)

(52) U.S. Cl.
CPC ................................... *H05B 47/16* (2020.01)

(58) Field of Classification Search
CPC ...... H05B 45/10; H05B 47/10; H05B 47/105; H05B 47/16
See application file for complete search history.

(56) References Cited

U.S. PATENT DOCUMENTS

| 9,410,664 B2 | 8/2016 | Krames et al. |
| 10,076,633 B2 | 9/2018 | Krames et al. |

(Continued)

FOREIGN PATENT DOCUMENTS

| JP | 2012-514829 A | 6/2012 |
| JP | 2015-097196 A | 5/2015 |
| WO | 2010/079388 A1 | 7/2010 |

OTHER PUBLICATIONS

Souman, J., et al., "Spectral Tuning of White Light Allows for Strong Reduction in Melatonin Suppression without Changing Illumination Level or Color Temperature", Journal of Biological Rhythms, (2018).

*Primary Examiner* — Jimmy T Vu
(74) *Attorney, Agent, or Firm* — Volpe Koenig (57) ABSTRACT

An illumination device includes a light emitter configured to emit illumination light and a controller configured to control the light emitter. The controller controls the illumination light such that a first decrease ratio of melanopic illuminance of illumination light during night-time illumination to melanopic illuminance of illumination light during daytime illumination is higher than a second decrease ratio of illuminance of the illumination light during the night-time illumination to illuminance of the illumination light during the daytime illumination.

15 Claims, 3 Drawing Sheets

(56) References Cited

U.S. PATENT DOCUMENTS

| | | |
|---|---|---|
| 10,137,277 B2 | 11/2018 | Krames et al. |
| 10,420,184 B1 | 9/2019 | Soler et al. |
| 10,900,615 B2 | 1/2021 | Krames et al. |
| 11,287,090 B2 | 3/2022 | Krames et al. |
| 11,725,783 B2 | 8/2023 | Krames et al. |
| 2015/0062892 A1 | 3/2015 | Krames et al. |
| 2018/0338359 A1 | 11/2018 | Soler |
| 2020/0332969 A1* | 10/2020 | Soler .................. H05B 45/20 |

* cited by examiner

ILLUMINATION DEVICE, ILLUMINATION SYSTEM, AND ILLUMINATION CONTROL METHOD

CROSS-REFERENCE TO RELATED APPLICATION

The present application claims priority of Japanese Patent Application No. 2020-26628 (filed in Feb. 19, 2020), the disclosure of which is incorporated herein in its entirety by reference.

TECHNICAL FIELD

The present disclosure relates to an illumination device, an illumination system, and an illumination control method.

BACKGROUND ART

Systems that control lighting in specific environments according to user preferences are known (see, for example, PTL 1).

CITATION LIST

Patent Literature

PTL 1: Japanese Unexamined Patent Application Publication (Translation of PCT Application) No. 2012-514829

SUMMARY OF INVENTION

An illumination device according to an embodiment of the present disclosure includes a light emitter configured to emit illumination light and a controller configured to control the light emitter. The controller controls the illumination light such that a first decrease ratio of a melanopic illuminance of illumination light during night-time illumination to a melanopic illuminance of illumination light during daytime illumination is higher than a second decrease ratio of an illuminance of the illumination light during the night-time illumination to an illuminance of the illumination light during the daytime illumination.

An illumination system according to an embodiment of the present disclosure includes an illumination device configured to emit illumination light and a server. The server controls the illumination light such that a first decrease ratio of a melanopic illuminance of illumination light during night-time illumination to a melanopic illuminance of illumination light during daytime illumination is higher than a second decrease ratio of an illuminance of the illumination light during the night-time illumination to an illuminance of the illumination light during the daytime illumination.

An illumination control method according to an embodiment of the present disclosure includes controlling illumination light by an illumination device including a light emitter configured to emit the illumination light. The illumination device controls the illumination light such that a first decrease ratio of a melanopic illuminance of illumination light during night-time illumination to a melanopic illuminance of illumination light during daytime illumination is higher than a second decrease ratio of an illuminance of the illumination light during the night-time illumination to an illuminance of the illumination light during the daytime illumination.

DESCRIPTION OF EMBODIMENTS

At present, a daily life without hindrance requires illumination in the night-time. Exposure of humans to light in the night-time may suppress melatonin secretion in the human body. Since melatonin is found to have an effect of regulating the rhythm of wakefulness and sleep, a vasodilatory effect, an antioxidant effect, and an anticancer effect, the suppression of melatonin secretion can affect human health.

The present disclosure describes an illumination device that can control illumination such that, while the circadian rhythm of the user is taken into consideration, the daily life of a user is less likely hindered.

Exemplary Configuration of Illumination Device

Figure 1:
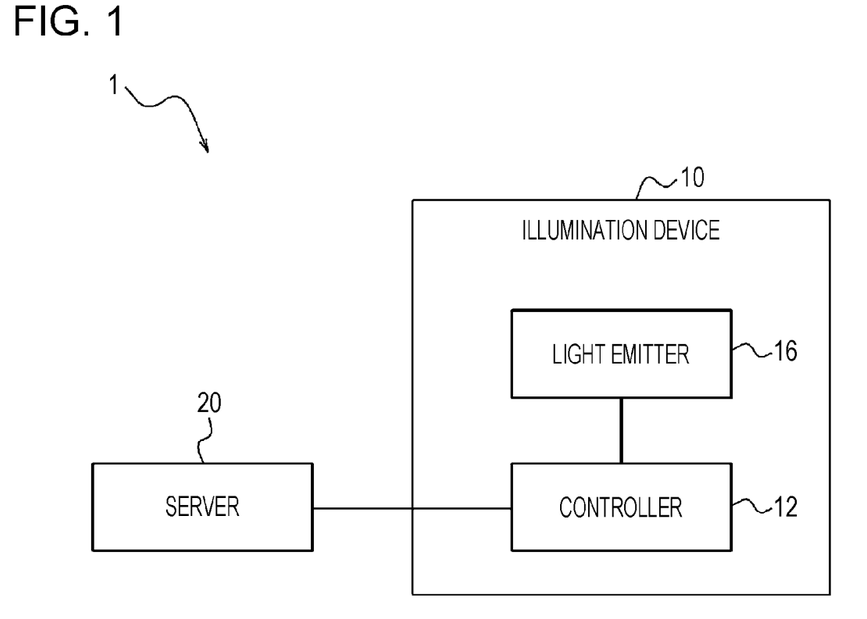
FIG. 1 is a block diagram illustrating exemplary configurations of an illumination system and an illumination device according to an embodiment.

As illustrated in FIG. 1, an illumination system 1 includes an illumination device 10 and a server 20.

The illumination device 10 includes a controller 12 and multiple light emitters 16. The light emitters 16 each emit light determined by a given spectrum. The given spectrum may have one or more peak wavelengths within a wavelength range of 360 nm to 780 nm. The light having a peak wavelength in the wavelength range of 360 nm to 780 nm is also referred to as visible light. The wavelength range of 360 nm to 780 nm is also referred to as the visible light range. In other words, the light emitter 16 may emit light determined by a spectrum having one or more peak wavelengths in the visible light range. The spectrum determining the light is measured by, for example, spectroscopy using a spectral photometer.

The light emitted by the light emitters 16 and added is referred to as combined light. The combined light is regarded as illumination light emitted by the entire illumination device 10. The spectrum of light emitted by at least one of the light emitters 16 differs from that of light emitted by the other light emitters 16. The controller 12 can control each of the light emitters 16 emitting light determined by a different spectrum and thereby control the spectrum of the illumination light emitted by the entire illumination device 10.

The controller 12 may include at least one processor to provide controlling and processing capabilities for executing various functions of the illumination device 10. The processor can execute a program achieving various functions of the controller 12. The processor may include a single integrated circuit. The integrated circuit may be abbreviated as IC. The processor may include multiple integrated circuits and discrete circuits that are communicably connected. The processor may be based on any other known technique.

The controller 12 may include a storage unit. The storage unit may include an electromagnetic storage medium, such as a magnetic disk, or may include a memory, such as a semiconductor memory or magnetic memory. The storage unit stores, for example, various types of information and programs executed by the controller 12. The storage unit may serve as a work memory of the controller 12. At least part of the storage unit may be separate from the controller 12.

The light emitters 16 may each include, for example, a light emitting element and a wavelength converting member. The light emitting element may emit light determined by a spectrum having a peak wavelength within a wavelength range of, for example, 360 nm to 430 nm. The light determined by the spectrum having a peak wavelength in the wavelength range of 360 nm to 430 nm is also referred to as violet light. The wavelength range of 360 nm to 430 nm is also referred to as the violet light range. Visible light includes the violet light. The visible light range includes the violet light range. The wavelength converting member converts light entered from the light emitting element into light determined by a spectrum having a peak wavelength in the visible light range and emits the converted light. In other words, the wavelength converting member is excited by the light emitted by the light emitting element and emits light with a different wavelength. The light emitted by the light emitting element is referred to as excitation light. The excitation light is not limited to the violet light and may be blue light or the like determined by a spectrum having a peak wavelength within a wavelength range of, for example, 430 nm to 500 nm.

The wavelength converting member may contain a phosphor. The phosphor may convert the excitation light into light determined by a spectrum having a peak wavelength within a wavelength range of, for example, 400 nm to 500 nm, in other words, into blue light. The phosphor may convert the excitation light into light determined by a spectrum having a peak wavelength within a wavelength range of, for example, 450 nm to 550 nm, in other words, into bluish-green light. The phosphor may convert the excitation light into light determined by a spectrum having a peak wavelength within a wavelength range of, for example, 500 nm to 600 nm, in other words, into green light. The phosphor may convert the excitation light into light determined by a spectrum having a peak wavelength within a wavelength range of, for example, 600 nm to 700 nm, in other words, into red light. The phosphor may convert the excitation light into light determined by a spectrum having a peak wavelength within a wavelength range of, for example, 680 nm to 800 nm, in other words, into near-infrared light. The phosphor may convert the excitation light into, for example, bright red light, yellow light, or white light.

The wavelength converting member may include multiple types of phosphors. The types of the phosphors are not limited to those described above, and any other type of phosphor may be contained. Combinations of the types of the phosphors contained in the wavelength converting member are not specifically limited. The proportion of the phosphors contained in the wavelength converting member is not specifically limited. The wavelength converting member converts the excitation light into light determined by a spectrum defined based on the types and proportions of the contained phosphors. The illumination device 10 may include light emitters 16 respectively emitting, for example, violet light, blue light, green light, bluish-green light, bright red light, yellow light, red light, and white light. The illumination device 10 controls intensities of light emitted by the respective light emitters 16 and thereby controls the spectrum of combined light.

The server 20 is communicably connected to the illumination device 10 in a wired or wireless manner. The server 20 may include at least one processor. The processor of the server 20 may be the same as or similar to that of the controller 12. The server 20, instead of the controller 12, may perform an operation related to control of the illumination light, which will be described below. The server 20 may transmit control instructions to the light emitters 16 through communication.

Melanopic Illuminance

Figure 2:
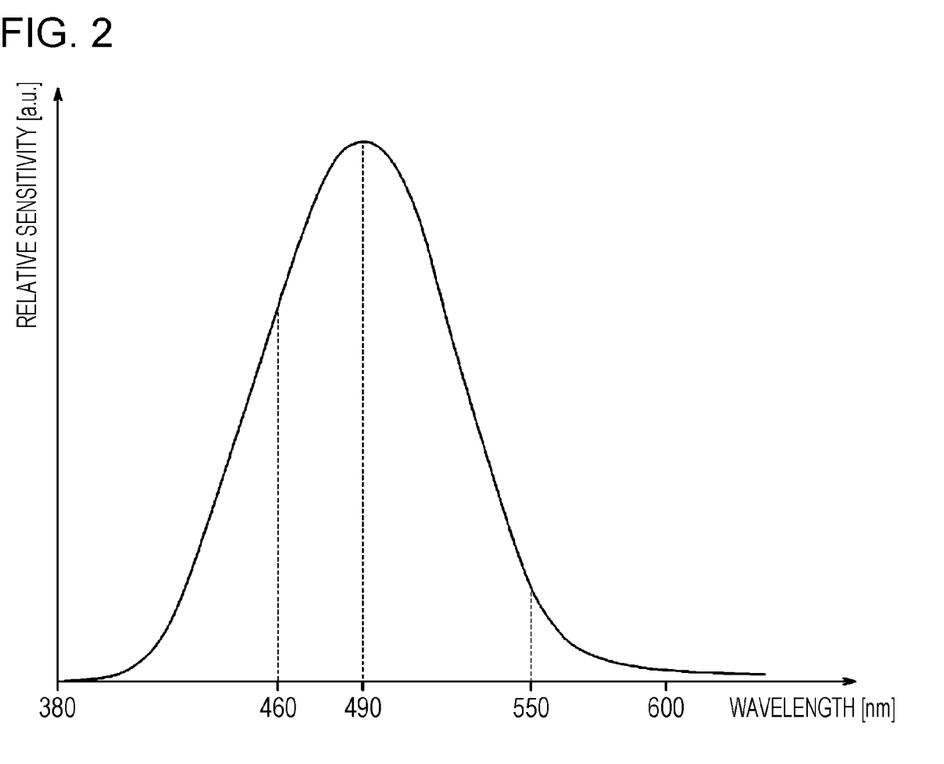
FIG. 2 is a graph showing an exemplary curve of spectral sensitivity of ipRGCs.

FIG. 2 shows a graph of spectral sensitivity of intrinsically photosensitive retinal ganglion cells (ipRGCs) contributing to melatonin secretion in the human body. In FIG. 2, the horizontal axis indicates wavelengths of light and the vertical axis indicates relative sensitivity of the ipRGCs at the wavelengths. The spectral sensitivity of the ipRGCs has a peak at a wavelength of about 490 nm.

According to <Paper 1> below, melatonin secretion in humans exposed to light is less than in humans in darkness. A reduction in melatonin secretion depends on the light wavelength. A reduction in melatonin secretion in humans exposed to light with a wavelength of 460 nm is larger than that in melatonin secretion in humans exposed to light with a wavelength of 550 nm. In other words, exposure of humans to light with a wavelength near the wavelength at which the spectral sensitivity of the ipRGCs has a peak leads to a large reduction in melatonin secretion in humans.

<Paper 1>

Cajochen C et al., J. Clin. Endocrinol. Metab., 2005; 90(3): 1311-1316

In <Paper 2> below, quantification of the effect of the spectrum of illumination light on the ipRGCs is attempted. In <Paper 2>, control of the spectrum of the illumination light so as to reduce the effect on the ipRGCs is proposed. For such control, it is proposed to control melanopic illuminance, determined according to the spectral sensitivity of the ipRGCs, as a parameter of the illumination light.

<Paper 2>

Robert J. Lucas et al., Trends in Neurosciences, January 2014, Vol. 37, No. 1

The melanopic illuminance can be calculated by using, for example, a spreadsheet provided by Lucas et al. downloadable at the following URL:

http://personalpages.manchester.ac.uk/staff/robert.lucas/Lucas%20et%20al%202014%20workbook.xls In the present embodiment, the melanopic illuminance is calculated mainly based on irradiance at each wavelength within a wavelength range of 400 nm to 550 nm.

Exemplary Control of Spectrum

The illumination device 10 according to the present embodiment can reduce the effect of the illumination light on human circadian rhythm by controlling the spectrum of the illumination light in reference to the melanopic illuminance as a parameter. Specifically, the illumination device 10 includes the light emitters 16 for emitting the illumination light and the controller 12 for controlling the light emitters 16. The controller 12 can control the melanopic illuminance of illumination light to decrease the melanopic illuminance of illumination light during the night-time illumination compared with the melanopic illuminance of illumination light during the daytime illumination. As a result, illumination light that reduces the effect on human circadian rhythm and hindrance to daily life can be achieved. Night-time may be, for example, from 19:00 to 24:00. Daytime may be, for example, from 10:00 to 12:00.

Illuminance

The illumination device 10 may control the spectrum of the illumination light in reference to illuminance of visible light as a parameter. The illuminance represents a measure of illumination of an object. In other words, the illumination device 10 can achieve the illumination light that reduces the effect on human circadian rhythm and hindrance to daily life by controlling the spectrum of the illumination light in reference to the illuminance and the melanopic illuminance as parameters.

The controller 12 can control the melanopic illuminance of the illumination light to decrease the illuminance of the illumination light during the night-time illumination compared with the illuminance of the illumination light during the daytime illumination. Accordingly, daily life can less likely be hindered by a variation in the spectrum of the illumination light.

The illumination device 10 may control the illumination light such that a decrease ratio of the melanopic illuminance of the illumination light during the night-time illumination to the melanopic illuminance of the illumination light during the daytime illumination is higher than a decrease ratio of the illuminance of the illumination light during the night-time illumination to the illuminance of the illumination light during the daytime illumination. The decrease ratio of the melanopic illuminance of the illumination light during the night-time illumination to the melanopic illuminance of the illumination light during the daytime illumination is also referred to as a first decrease ratio. The decrease ratio of the illuminance of the illumination light during the night-time illumination to the illuminance of the illumination light during the daytime illumination is also referred to as a second decrease ratio. In other words, the second decrease ratio is lower than the first decrease ratio. A decrease ratio is expressed by division of a decrease in a parameter from an original value thereof by the original value. As a result, the illumination device 10 reduces the effect of a decrease in melanopic illuminance on the illuminance. The reduced effect on the illuminance reduces hindrance to daily human life. Meanwhile, a decrease in melanopic illuminance less likely suppress melatonin secretion in humans during the night-time. As a result, the effect on human circadian rhythm is reduced. In other words, a reduction in the effect on the circadian rhythm is compatible with a reduction in hindrance to daily life. The illumination device 10 may control the spectrum of the illumination light during the night-time so as to decrease the melanopic illuminance while maintaining the illuminance as a parameter of the illumination light.

Photon Flux

The illumination device 10 may control photon flux as a parameter of the illumination light. Photon flux represents the number of photons per second and $cm^2$. Accordingly, daily life can less likely be hindered by a variation in the spectrum of the illumination light. In other words, the illumination device 10 can achieve the illumination light that reduces the effect on human circadian rhythm and hindrance to daily life by controlling the spectrum of the illumination light in reference to the photon flux and the melanopic illuminance as parameters.

The controller 12 can control the photon flux of the illumination light and decrease the photon flux of the illumination light during the night-time illumination compared with the photon flux of the illumination light during the daytime illumination. Accordingly, daily life can less likely be hindered by a variation in the spectrum of the illumination light.

The illumination device 10 may control the illumination light such that the first decrease ratio of the melanopic illuminance of the illumination light during the night-time illumination to the melanopic illuminance of the illumination light during the daytime illumination is higher than a decrease ratio of the color temperature of the illumination light during the night-time illumination to the color temperature of the illumination light during the daytime illumination. The decrease ratio of the color temperature of the illumination light during the night-time illumination to the color temperature of the illumination light during the daytime illumination is also referred to as a third decrease ratio. In other words, the third decrease ratio is lower than the first decrease ratio. This enables humans to have a reduced sense of discomfort. The illumination device 10 may control the spectrum of the illumination light during the night-time so as to decrease the melanopic illuminance while maintaining the photon flux as a parameter of the illumination light.

When decreasing the melanopic illuminance, the illumination device 10 may control the illumination light such that not only the second decrease ratio of the illuminance but also the third decrease ratio of the photon flux are lower than the first decrease ratio of the melanopic illuminance. The illumination device 10 may decrease the melanopic illuminance while maintaining both the illuminance and the photon flux as parameters of the illumination light.

Color Temperature

The illumination device 10 may control color temperature as a parameter of the illumination light. Color temperature is a parameter corresponding to the temperature of a black body. T represents a color temperature of a spectrum of light radiated by a black body having a temperature denoted by T. For example, the color temperature of a spectrum of light radiated by a black body having a temperature of 5000 kelvins (K) is represented as 5000 K. The color of light having a color temperature of about 4000 to 5000 K is referred to as white. Light having a lower color temperature than white light can contain a higher proportion of the red component in the color. In other words, light having a low color temperature looks reddish. Light having a higher color temperature than white light can contain a higher proportion of the blue component in the color. In other words, light having a high color temperature looks bluish.

Not only a spectrum of light radiated by a black body but also a spectrum approximate to that of the light radiated by a black body may be represented by color temperature. In the case that a given spectrum approximates to the spectrum of the light radiated by a black body having a temperature denoted by T, the color temperature of the given spectrum is also denoted by T. Whether the two spectra of light are in a mutually approximate relationship may be determined under various conditions. The conditions for the two spectra of light to be in a mutually approximate relationship may include, for example, a condition that a comparison of relative intensities of the two spectra of light at wavelengths of the spectra exhibits a difference between the relative intensities being in a given range at every wavelength. The conditions for the two spectra of light to be in a mutually approximate relationship may include, for example, a condition that a difference between peak wavelengths of the two spectra of light is in a given range. The conditions for the two spectra of light to be in a mutually approximate relationship are not limited to these examples and may include any other condition.

For example, the spectrum of sunlight around noon can be approximated to that of light radiated by a black body having a temperature of about 5000 K. In this case, the color temperature of sunlight around noon is represented as about 5000 K. The color of light represented by a color temperature of about 5000 K is referred to as neutral white. A color of light having a higher color temperature than neutral white, i.e., a color temperature of about 6500 K, is referred to as daylight color. Daylight color contains a higher proportion of a blue light component than neutral white or a component having a shorter wavelength than blue light and looks bluish. In contrast, neutral white looks closer to white than the daylight color.

The illumination device 10 enables, by controlling the color temperature, daily life to be less likely hindered by a variation in the spectrum of the illumination light. In other words, the illumination device 10 can achieve the illumination light that reduces the effect on human circadian rhythm and hindrance to daily life by controlling the spectrum of the illumination light in reference to the color temperature and the melanopic illuminance as parameters.

The controller 12 can control the color temperature of the illumination light such that the color temperature of the illumination light during the night-time illumination is lower than the color temperature of the illumination light during the daytime illumination. Accordingly, daily life can less likely be hindered by a variation in the spectrum of the illumination light.

The illumination device 10 may control the illumination light such that the first decrease ratio of the melanopic illuminance of the illumination light during the night-time illumination to the melanopic illuminance of the illumination light during the daytime illumination is higher than a decrease ratio of the photon flux of the illumination light during the night-time illumination to the photon flux of the illumination light during the daytime illumination. The decrease ratio of the photon flux of the illumination light during the night-time illumination to the photon flux of the illumination light during the daytime illumination is also referred to as a fourth decrease ratio. In other words, the fourth decrease ratio may be lower than the first decrease ratio. This can reduce an unexpected effect on a human. The illumination device 10 may control the spectrum of the illumination light in the night-time so as to decrease the melanopic illuminance while maintaining the color temperature as a parameter of the illumination light.

When decreasing the melanopic illuminance, the illumination device 10 may control not only the second decrease ratio of the illuminance but also the fourth decrease ratio of the color temperature such that the second and fourth decrease ratios are lower than the first decrease ratio of the melanopic illuminance. The illumination device 10 may decrease the melanopic illuminance while maintaining both of the illuminance and the color temperature as parameters of the illumination light.

Comparative Example

The illumination device 10 according to the present embodiment includes the light emitters 16 for emitting various colors and thus enables emission of light determined by various spectra. In contrast, a device according to a comparative example includes a light emitting element for emitting blue light and a phosphor for converting the blue light into yellow light.

Figure 3:
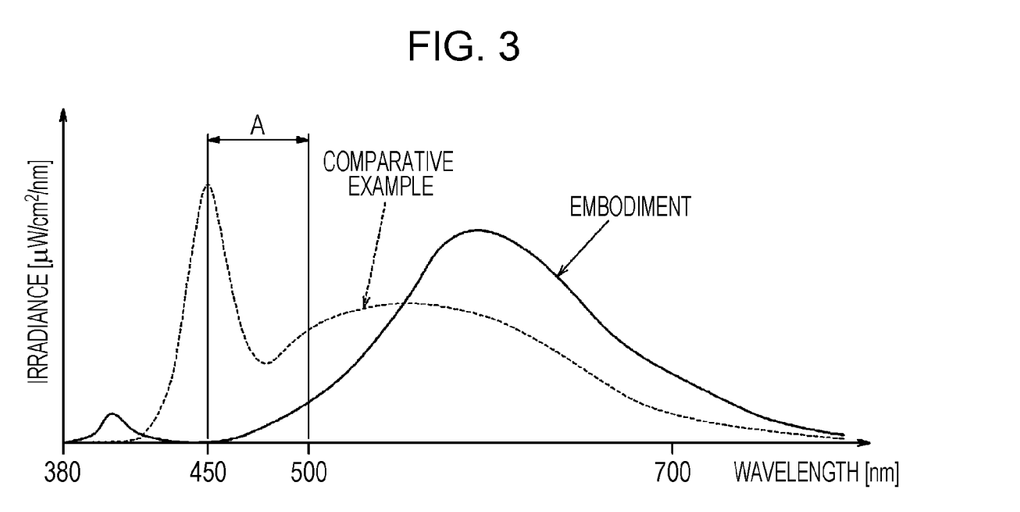
FIG. 3 is a graph showing an exemplary spectrum where illuminance and photon flux are maintained while melanopic illuminance is decreased.
Figure 4:
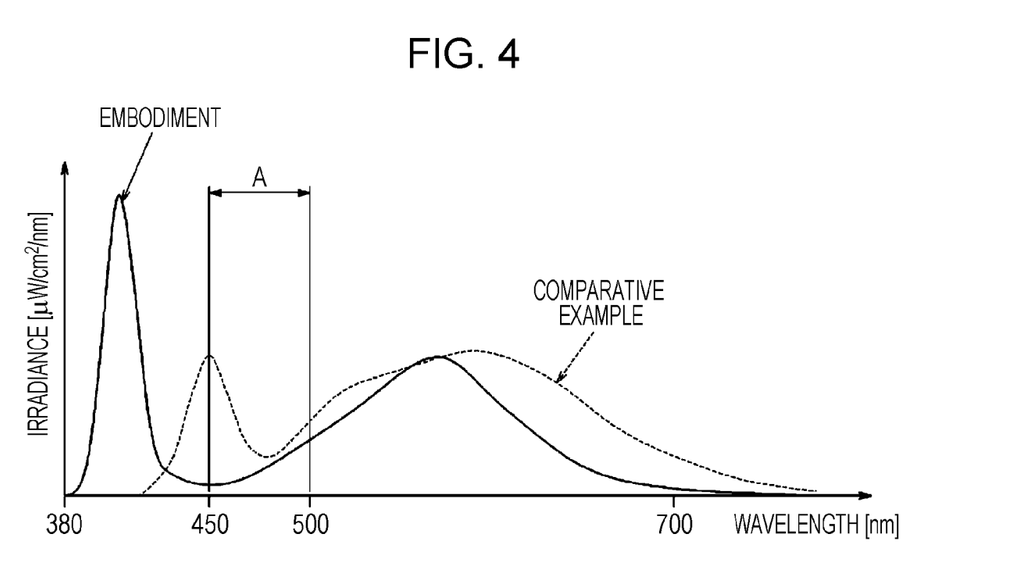
FIG. 4 is a graph showing an exemplary spectrum where the illuminance and color temperature are maintained while the melanopic illuminance is decreased.

In FIGS. 3 and 4, a spectrum determining illumination light emitted by the illumination device 10 according to the present embodiment is compared with a spectrum determining illumination light emitted by the device according to the comparative example. In FIGS. 3 and 4, the horizontal axis indicates a wavelength of the illumination light. The vertical axis indicates irradiance of light with each wavelength. The spectrum determining the illumination light emitted by the illumination device 10 according to the present embodiment is indicated by a solid line. The spectrum determining the light emitted by the device according to the comparative example is indicated by a dashed line.

As illustrated in FIG. 3, the spectrum of the illumination light according to the present embodiment is quite different from the spectrum of the illumination light according to the comparative example. The illumination light according to the present embodiment has an illuminance of 158.5 lux. The illumination light according to the comparative example has an illuminance of 158.5 lux. The illumination light according to the present embodiment has a photon flux of 1.45E+14 photons/cm$^2$/s. The illumination light according to the comparative example has a photon flux of 1.45E+14 photons/cm$^2$/s. In other words, the illumination light according to the present embodiment has the same illuminance and the same photon flux as the illumination light according to the comparative example.

Meanwhile, there is a quite difference between the illumination light according to the present embodiment and the illumination light according to the comparative example regarding irradiance at wavelengths in a wavelength range of 450 nm to 500 nm, which contributes greatly to the melanopic illuminance. The wavelength range of 450 nm to 500 nm corresponds to a range indicated by arrow A. The irradiance of the spectrum determining the illumination light within the range indicated by arrow A according to the present embodiment is lower than the irradiance of the illumination light according to the comparative example. The illumination light according to the present embodiment has a melanopic illuminance of 40 melanopic lux. The illumination light according to the comparative example has a melanopic illuminance of 157 melanopic lux. The melanopic illuminance is an illuminance weighted with the spectral sensitivity of ipRGCs and "lux" may be used simply as its unit in some cases. In other words, the illumination light according to the present embodiment has a lower melanopic illuminance than the illumination light according to the comparative example.

As described above, the illumination device 10 can decrease the melanopic illuminance while maintaining the illuminance and the photon flux, compared with the illumination light according to the comparative example.

As illustrated in FIG. 4, the spectrum of the illumination light according to the present embodiment is quite different from the spectrum of the illumination light according to the comparative example. The illumination light according to the present embodiment has an illuminance of 159.6 lux. The illumination light according to the comparative example has an illuminance of 159.3 lux. The illumination light according to the present embodiment has a color temperature of 3930 K. The illumination light according to the comparative example has a color temperature of 3942 K. In other words, the illumination light according to the present embodiment has substantially the same illuminance and the same color temperature as those of the illumination light according to the comparative example.

Meanwhile, there is a quite difference between the illumination light according to the present embodiment and the illumination light according to the comparative example regarding irradiance at wavelengths in a wavelength range of 450 nm to 500 nm. The wavelength range of 450 nm to 500 nm corresponds to a range indicated by arrow A. The irradiance of the spectrum determining the illumination light within the range indicated by arrow A according to the present embodiment is lower than the irradiance of the illumination light according to the comparative example. The illumination light according to the present embodiment has a melanopic illuminance of 78 melanopic lux. The illumination light according to the comparative example has a melanopic illuminance of 106 melanopic lux. In other words, the illumination light according to the present embodiment has a lower melanopic illuminance than the illumination light according to the comparative example.

As described above, the illumination device 10 can decrease the melanopic illuminance while maintaining the illuminance and the color temperature, compared with the illumination light according to the comparative example.

Variation in Illumination Light Over Time

Figure 5:
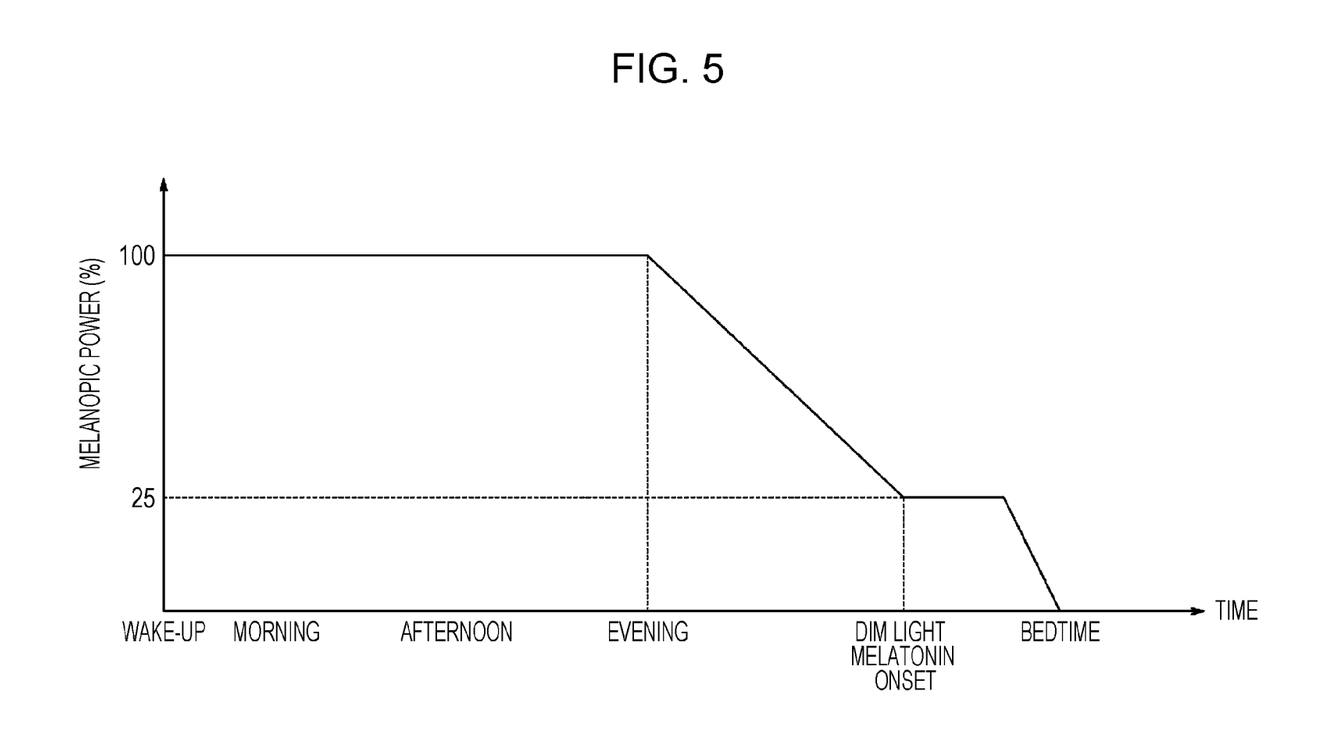
FIG. 5 is a graph showing an example where the melanopic illuminance of illumination light is varied with the lapse of time.

As illustrated in FIG. 5, the illumination device 10 may vary the melanopic illuminance of the illumination light with the lapse of time. In the graph in FIG. 5, the horizontal axis indicates a time elapsed from awaking to sleeping of a subject exposed to illumination by the illumination device 10. The vertical axis indicates melanopic power. The melanopic power is a value represented as a ratio of an actual melanopic illuminance of the illumination light emitted by the illumination device 10 to a maximum melanopic illuminance of the illumination light emitted by the illumination device 10. The maximum melanopic illuminance corresponds to a total melanopic illuminance of the illumination light emitted from all the light emitters 16 of the illumination device 10 at maximum output power. Thus, the melanopic power has a maximum value of 100%.

The illumination device 10 may determine the melanopic power as 100% from awaking of the subject until the evening. The evening corresponds to a time period between daytime and night-time or a time between daytime and night-time. The illumination device 10 may determine the melanopic power as a value of less than 100%. The illumination device 10 controls the spectrum of the illumination light at dim light melatonin onset (DLMO) such that the melanopic power has a given value or less. Accordingly, the circadian rhythm of the subject is less affected.

While determining the melanopic power as a given value or less, the illumination device 10 may determine the decrease ratio of the illuminance of the illumination light being lower than the decrease ratio of the melanopic illuminance of the illumination light. This reduces hindrance to the daily life of the subject.

The illumination device 10 may quickly decrease the melanopic power to a given value or less at dim light melatonin onset.

The illumination device 10 may start to decrease the melanopic power at a given time before dim light melatonin onset. The illumination device 10 may gradually decrease the melanopic power from, for example, the evening until dim light melatonin onset. Thereby, the subject is less likely to notice a variation in illumination light.

In the example in FIG. 5, the melanopic power is determined as a given value of 25%. The given value is not limited to 25% and may be determined as any other value.

Dim light melatonin onset may be determined as, for example, a time at which melatonin secretion in the subject exceeds a given value (e.g., 3 pg/ml). Dim light melatonin onset may be determined as a time at which melatonin secretion exceeds two times a standard deviation of the melatonin secretion calculated from at least three pieces of data: the data is acquired from at least three measurement times (for example, measurement every 30 minutes) until a given time before bedtime of the subject (for example, two hours before). Dim light melatonin onset may be determined according to an individual difference or a difference in body condition.

The illumination device 10 may determine the melanopic power as 0% or turn off at bedtime of the subject.

As described above, the illumination device 10 according to the present embodiment can control the illumination light such that, while the circadian rhythm of a user is taken into consideration, the user can live without hindrance.

Illumination Control Method

The illumination device 10 may carry out an illumination control method including a step, which will be exemplified below. The illumination control method may be carried out by the server 20. The illumination control method may be achieved by an illumination control program causing a processor to execute illumination control. The illumination control program may be stored in a non-transitory computer readable medium. The illumination control program may be executed by a processor of the server 20.

Step

The illumination device 10 controls the illumination light such that the first decrease ratio of the melanopic illuminance of the illumination light during the night-time illumination to the melanopic illuminance of the illumination light during the daytime illumination is higher than the second decrease ratio of the illuminance of the illumination light during the night-time illumination to the illuminance of the illumination light during the daytime illumination.

The illumination device 10 can control the illumination light by carrying out the aforementioned step such that, while the circadian rhythm of a user is taken into consideration, the user can live without hindrance.

The drawings describing the embodiment according to the present disclosure are schematic. For example, dimensional ratios of the drawings are not necessarily correspond to those in reality.

Although the embodiment according to the present disclosure has been described with reference to the drawings and examples, it should be noted that a person skilled in the art can make various modifications or alterations based on the disclosure. Thus, it should be noted that these modifications or alterations fall within the scope of the present disclosure. For example, functions of components can be reordered so as not to logically conflict with each other, and such components can be combined into one or divided.

REFERENCE SIGNS LIST 1 illumination system
10 illumination device
12 illumination controller 16 light emitters
20 server

The invention claimed is:

1. An illumination device comprising:
    a light emitter configured to emit illumination light; and
    a controller configured to control the light emitter,
    wherein the controller controls the illumination light such that a first decrease ratio of a melanopic illuminance of illumination light during night-time illumination to a melanopic illuminance of illumination light during daytime illumination is higher than a second decrease ratio of an illuminance of the illumination light during the night-time illumination to an illuminance of the illumination light during the daytime illumination.

2. The illumination device according to claim 1, wherein the controller controls the illumination light such that the illuminance of the illumination light during the night-time illumination is lower than the illuminance of the illumination light during the daytime illumination.

3. The illumination device according to claim 1, wherein the controller controls the illumination light such that the first decrease ratio is higher than a third decrease ratio of a color temperature of the illumination light during the night-time illumination to a color temperature of the illumination light during the daytime illumination.

4. The illumination device according to claim 1, wherein the controller controls the illumination light such that a color temperature of the illumination light during the night-time illumination is lower than a color temperature of the illumination light during the daytime illumination.

5. The illumination device according to claim 1, wherein the controller controls the illumination light such that the first decrease ratio is higher than a fourth decrease ratio of a photon flux of the illumination light during the night-time illumination to a photon flux of the illumination light during the daytime illumination.

6. The illumination device according to claim 1, wherein the controller controls the illumination light such that a photon flux of the illumination light during the night-time illumination is lower than a photon flux of the illumination light during the daytime illumination.

7. The illumination device according to claim 1, wherein the controller determines, based on dim light melatonin onset, timing of decreasing the melanopic illuminance.

8. The illumination device according to claim 1, wherein the controller controls the illumination light such that melanopic power has a given value or less at dim light melatonin onset.

9. The illumination device according to claim 1, wherein the controller controls the illumination light such that melanopic power starts to decrease at a given time before dim light melatonin onset.

10. The illumination device according to claim 1, wherein the controller controls the illumination light by determining, as the dim light melatonin onset, a time at which melatonin secretion exceeds a given value.

11. The illumination device according to claim 1, wherein the controller controls the illumination light by determining, as the dim light melatonin onset, a time at which melatonin secretion in a subject exceeds two times a standard deviation of the melatonin secretion calculated from data, the data being acquired from at least three measurement times of the melatonin secretion until a given time before bedtime of the subject.

12. The illumination device according to claim 1, wherein the controller determines melanopic power as a given value or less while determining a decrease ratio of the illuminance of the illumination light being lower than a decrease ratio of the melanopic illuminance of the illumination light.

13. The illumination device according to claim 1, wherein the controller determines melanopic power as 0% at bedtime of a subject.

14. An illumination system comprising a server and an illumination device configured to emit illumination light,
    wherein the server controls the illumination light such that a first decrease ratio of a melanopic illuminance of illumination light during night-time illumination to a melanopic illuminance of illumination light during daytime illumination is higher than a second decrease ratio of an illuminance of the illumination light during the night-time illumination to an illuminance of the illumination light during the daytime illumination.

15. An illumination control method, comprising:
    controlling, by an illumination device comprising a light emitter configured to emit illumination light, the illumination light emitted by the light emitter such that a first decrease ratio of a melanopic illuminance of illumination light during night-time illumination to a melanopic illuminance of illumination light during daytime illumination is higher than a second decrease ratio of an illuminance of the illumination light during the night-time illumination to an illuminance of the illumination light during the daytime illumination.

* * * * *